United States Patent [19]

Clark et al.

[11] 4,367,233

[45] Jan. 4, 1983

[54] INHIBITORS OF MAMMALIAN COLLAGENASE

[75] Inventors: Donald E. Clark, Norristown; Norman H. Grant, Wynnewood, both of Pa.

[73] Assignee: American Home Products Corporation, New York, N.Y.

[21] Appl. No.: 307,711

[22] Filed: Oct. 2, 1981

[51] Int. Cl.³ .................. A61U 31/44; A61U 31/425
[52] U.S. Cl. .................................. 424/270; 424/263
[58] Field of Search ........................................ 424/270

[56] References Cited

U.S. PATENT DOCUMENTS 4,294,839 10/1981 Doll ..................................... 548/170

Primary Examiner—Stanley J. Friedman
Attorney, Agent, or Firm—George Tarnowski

[57] ABSTRACT

A method of inhibiting mammalian collagenase by using α-phenyl-2-(aza)benzothiazolylthioglycolic acids and derivatives thereof, and the pharmaceutically acceptable salts thereof.

13 Claims, No Drawings

INHIBITORS OF MAMMALIAN COLLAGENASE

BACKGROUND OF THE INVENTION

Collagen is the major organic component of the surface tissue found in the cornea, skin, gastro-intestinal viscera, joint mucosa and other areas of the body. The collagen molecule has a molecular weight of 300,000, and is composed of three helical polypeptide chains which are wound around a common axis forming a coiled chain. In solution collagen molecules exist as long rods about 3000×15 A, but at a temperature of 37° C. and a pH of 7, the molecules polymerize into insoluble fibrils. Thus, it is as fibrils that collagen invariably exists in tissue. The helical structure of undenatured collagen is remarkably resistant to attack by proteolytic enzymes; however, there have been discovered a number of natural enzymes, i.e., animal collagenases, which are capable of breaking down collagen by cleaving the collagen molecule across the helical backbone yielding ¾ and ¼ length fragments.

The relationship between collagenase and the destruction of collagen-based tissue has been found in a number of disease states affecting various parts of the body, all of which are basically similar in that collagen constitutes the major organic component, e.g., skin, cornea, gastro-intestinal viscera, joint mucosa, etc. For example, in connection with corneal tissue, it has been shown that collagenase is responsible for ulcers appearing after the eye has been burned with alkali. Similarly, the relationship exists for other ulcerous conditions of the cornea such as viral ulcers, e.g., herpes simplex, vaccinia, etc.; bacterial ulcers, e.g. Pseudomonas, etc.; degenerative ulcers and ulcers of unknown origin, e.g., associated with rheumatoid arthritis, Mooren's ulcer, furrow ulcer; and ulcers secondary to drying, e.g. erythema multiforme (Stevens-Johnson Syndrome).

In mammals, collagenase is one of the key enzymes involved in the cartilage and joint destruction of rheumatoid arthritis; see, for example, *Arthritis and Rheumatism*, 20 (6): 1231 (1977). The action of mammalian collagenase has also been implicated as a causative factor in several other diseases in mammals. These diseases include periodontal disease, tumor invasiveness, and epidermolysis bullosa; see, for example, *American Journal of Pathology*, 92 (2): 509 (1978) and *The New England Journal of Medicine*, 291 (13): 652 (1974).

Accordingly, collagenase inhibitors can be advantageously used to block pathologies in which destruction of collagenous connective tissue plays a central role, such as for example, periodontal disease, rheumatoid arthritis, corneal ulcerations, and so forth.

DESCRIPTION OF THE INVENTION

The present invention is directed to a method of inhibiting mammalian collagenase in mammals afflicted with a disease state in which collagen is broken down by collagenase which comprises administering to such an afflicted mammal an amount sufficient to reverse said collagenase-induced collagen breakdown of a collagenase inhibitor having the formula:

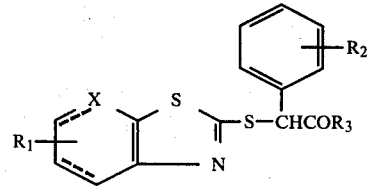

wherein $R_1$ is hydrogen, halo, nitrio, amino, lower alkyl, lower alkoxy, trifluoromethyl or hydroxy; $R_2$ is fluorine, chlorine, bromine, lower alkyl lower alkoxy, amino, nitro or trifluoromethyl; $R_3$ is hydroxy, lower alkoxy, amino, hydroxy(lower)alkyl amino, N-(lower-)alkanoylamino(lower)alkoxy or N-arylcarbamoyl(lower)alkylthio; X is CH or N, and where the dotted lines represent optional double bonds in the 5,6 and 7,8 positions, and the pharmacologically acceptable salts thereof.

The compounds of formula I and their method of preparation are disclosed in pending U.S. Ser. No. 273,826.

The term "lower alkyl" when used herein includes straight and branched chain hydrocarbon radicals having from 1 to about 6 carbon atoms. The terms "lower alkoxy" and "lower alkanoyl" in like manner designate radicals in which the hydrocarbon portion has 1 to about 6 carbon atoms.

The terms "halo" and "halide" when used herein refer to radicals of the elements fluorine, chlorine and bromine and chlorine and bromine, respectively.

The term pharmaceutically acceptable salts includes the salts pharmacologically-acceptable organic and inorganic acids such as hydrochloric, hydrobromic, sulfuric, nitric, phosphoric, methanesulfonic, benzenesulfonic and the like, alkali metal carboxylates and carboxylates of a pharmacologically acceptable cation derived from ammonia or a basic amine.

The compounds used in the invention can be readily prepared according to the following reaction sequence:

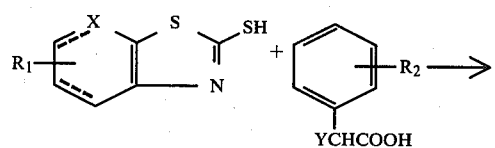

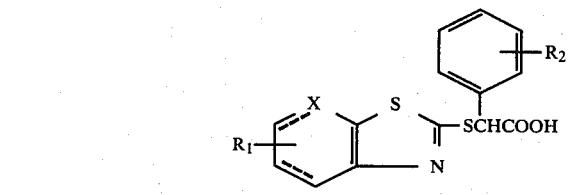

wherein $R_1$, $R_2$, X, Y and the dotted lines are as defined hereinbefore. The reaction of the appropriately substituted 2-mercapto (aza)benzothiazole and the α-halophenylacetic acid is carried out in an organic solvent, such as for example acetone and can be performed at room temperature or at elevated temperatures. The substituted-2-mercapto(aza)benzothiazoles can be reacted in their alkali metal or alkaline earth metal salt form. The reaction can also be carried out in the presence of a scavenging agent for the liberated hydrohalide, such as a tertiary amine, for example triethylamine. This is preferred in the preparation of the azabenzothiazolylthioglycolic acids.

The derivatives of the α-phenyl-2-(aza)-benzothiazolylthioglycolic acids of the invention are most conveniently prepared by reacting the tricyclic mesoionic didehydro compounds disclosed in U.S. Pat. No. 4,275,065 with appropriate nucleophilic reactants. This reaction, involving the ring cleavage of the terminal thiazole ring, is as follows:

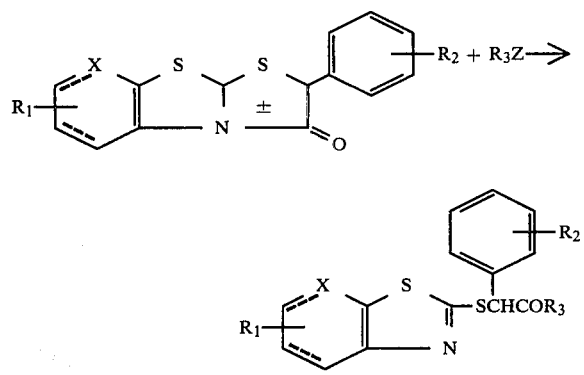

wherein $R_1$, $R_2$, $R_3$, and X are as described hereinbefore and $R_3Z$ is a nucleophilic reactant bearing the desired $R_3$ substituent. The reaction is carried out in a suitable organic solvent, such as for example methylene chloride and over a range of temperatures, such as room temperature as well as under reflux conditions, depending on the nature of the nucleophilic reactant being used.

The term "pharmacologically acceptable carrier" contemplates usual and customary substances employed to formulate solid, oral unit dosages for pharmacological purposes, including in its broadest form animal feedstuff. It also includes those employed to formulate either in unit dose or multidose form, oral and injectable suspensions and solutions, either directly or for reconstitution before administration.

To formulate dosages for administration according to this invention the compounds of formula I can be compounded into oral dosage forms such as tablets, capsules and the like. This is done by combining the compounds with conventional carriers, such as magnesium carbonate, magnesium stearate, talc, sugar, lactose, pectin, dextrin, starch, gelatin, tragacanth, methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The active ingredient may be encapsulated with or without other carriers. In all cases the proportion of active ingredients in said compositions both solid and liquid will be at least sufficient to impart collagenase inhibitory activity thereto on oral or parenteral administration.

In practicing the method of the invention, the instant compositions can be administered to warm-blooded animals, e.g., mice rats, rabbits, dogs, horses, monkeys, anthropoid apes, and the like, in a variety of dosage forms, alone or in combination with pharmacologically effective carriers, preferably orally or by injection.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effects.

The ability of the compounds of the invention to inhibit collagenase is demonstrated by testing in an enzyme assay using collagenase produced by normal human leukocytes or by normal human fibroblasts in culture.

The following examples show the preparation and testing of some of the compounds used in the invention.

EXAMPLE 1

α-(2-Benzothiazolylthio)benzeneacetic acid

A. α-(2-Benzothiazolylthio)benzene acetic acid, hydrobromide

A solution of 16.7 g (0.10 m) 2-mercaptobenzothiazole and 21.5 g (0.10 m) α-bromo-α-phenylacetic acid in acetone is heated to reflux for 5 hours and the solvent is then removed. The residual oil is triturated in acetone and 31 g of solid collected. The compound melts at 192°–4° C.

Analysis for: $C_{15}H_{11}NO_2S_2HBr$; Calculated: C, 47.12; H, 3.17; N, 3.66; Br, 20.90; S, 16.77; Found: C, 47.22; H, 3.06; N, 3.69; Br, 20.93; S, 16.73.

B. α-(2-Benzothiazolylthio)benzene acetic acid

The hydrobromide salt of A above is stirred in water at room temperature overnight, the solid collected and air dired. The crude material is recrystallized from acetonitrile to give the title compound in 70% yield and melting at 152°–4° C.

Analysis for: $C_{15}H_{11}NO_2S_2$; Calculated: C, 59.78; H, 3.68; N, 4.65; Found: C, 59.81; H, 3.85; N, 4.77.

EXAMPLE 2

α-(5-Chlorobenzothiazol-2-ylthio)benzene acetic acid 50.0 g (0.248 m) 5-chloro-2-mercaptobenzothiazole and 53.0 g (0.248 m) α-bromophenylacetic acid are dissolved in 1.5 l acetone and the solution is heated for 4 hours in the presence of 50 ml glacial acetic acid. The solution is concentrated to a smaller volume (about 200 ml) and the residual solid (90 g) is collected. The resulting salt is suspended in 1 l of water and the mixture is stirred at room temperature overnight. The collected solid is recrystallized from 2.5 l acetonitrile to give a total of 64 g (85% yield) of title compound melting at 190°–2° C.

Analysis for: $C_{15}H_{10}ClNO_2S_2$; Calculated: C, 53.64; H, 3.00; N, 4.17; Found: C, 53.83; H, 3.13; N, 4.13.

EXAMPLE 3

Sodium salt of α-(5-chlorobenzothiazol-2-ylthio)benzene acetic acid

To a solution of 10 g (0.03 m) of the compound of Example 2 in 600 ml of acetone is added an alcoholic NaOH (1.2 g) (0.03 m) in 20 ml ethanol)solution. The precipitate is collected and recrystallized from water. 8.0 g (71% yield) of title compound is isolated as a monohydrate melting at 238°–42° C. (dec.).

Analysis for: $C_{15}H_9ClNO_2S_2NaH_2O$; Calculated: C, 47.93; H, 2.95; N, 3.73; Found: C, 47.7; H, 3.12; N, 3.79.

EXAMPLE 4

α-(5-chlorobenzothiazol-2-ylthio)-α-(p-chlorophenyl)acetic acid

Method A. An acetone solution of 12.1 g (0.06 m) 5-chloro-2-mercaptobenzothiazole and 15.0 g (0.06 m) α-bromo-α-(p-chlorophenyl)acetic acid is heated in the presence of 30 ml glacial acetic acid for 5 hours. After solvent removal, the residual solid is collected. This solid (9 g of the hydrobromide salt of the title compound) is stirred in water overnight and the solid is collected and air dried. The crude material is recrystallized from acetonitrile to give 4.7 g (21% yield) of the title compound melting at 157°-8° C.

Method B. An acetone solution of the potassium salt of 5-chloro-2-mercaptobenzothiazole (0.05 m) and α-bromo-α-(p-chlorophenyl)acetic acid (0.05 m) are heated to reflux for 3 days. The solid (KBr), formed during the reaction, is filtered off and the filtrate is concentrated, and the residual solid triturated with a mixture of acetone and hexane. The crude material is recrystallized from benzene to give 7.7 g (42% yield) of title compound melting at 157°-8° C.

Method C. A methylene chloride solution of 10.0 g (0.05 m) 5-chloro-2-mercaptobenzothiazole, 12.5 g (0.05 m) α-bromo-α-(p-chlorophenyl)acetic acid and 10.0 g (0.10 m) triethylamine is heated to reflux overnight. The reaction mixture is washed first with a dilute hydrochloric acid solution, then with water and finally dried over $MgSO_4$. After the methylene chloride is removed, the residual solid is triturated with acetonitrile to give 13.6 g (74% yield) of title compound melting at 157°-8° C.

Analysis for: $C_{15}H_9Cl_2NO_2S_2$; Calculated: C, 48.65; H, 2.45; N, 3.78; Found: C, 48.69; H, 2.58; N, 3.79.

EXAMPLE 5

α-(p-Chlorophenyl)-A-(benzothiazol-2-yl-thio) acetic acid

Following the procedure of Example 4, Method C and substituting 2-mercaptobenzothiazole for 5-chloro-2-mercaptobenzothiazole, the title compound is prepared in 34% yield and having a melting point of 185°-7° C. (dec.)

Analysis for: $C_{15}H_{10}ClNO_2S_2$; Calculated: C, 53.64; H, 3.00; N, 4.17; Found: C, 54.07; H, 3.17; N, 4.13.

EXAMPLE 6

Preparation of 6-Chloro-2-phenylthiazolo [2,3-b]benzothiazol-3(2H)-one-mesoionic didehydro derivative 31 g (0.092 m) of the compound of Example 2 is suspended in 3.5 l methylene chloride and the mixture is heated to gentle reflux in the presence of 25 ml acetic anhydride. The solid is gradually dissolved, the solution turning reddish. After heating overnight, the solution is filtered and concentrated to 200 ml. The residual orange solid, weighing 29.5 g (quantitative yield) is collected and has a melting point of 215°-6° C.

EXAMPLE 7

α-(5-Chlorobenzothiazol-2-ylthio) benzene acetic acid 7 g of the compound of Example 6 is dissolved in 100 ml N,N-dimethylacetamide and the solution is allowed to stand at room temperature for 2 days in the presence of 5 ml water. The solution is diluted with 120 ml water and the resulting solid is collected and air dried. The crude material is recrystallized from 500 ml benzene. 5.9 g (80% yield) of purified title compound is obtained, having a melting point of 190°-1° C.

Analysis for: $C_{15}H_{10}ClNO_2S_2$; Calculated: C, 53.64; H, 3.00; N, 4.17; Found: C, 53.83; H, 3.13; N, 4.13.

EXAMPLE 8

α-(5-Chloro-2-benzothiazolylthio)benzene acetic acid, ethyl ester 8.0 g of the compound of Example 6 is dissolved in ethanol and the solution is warmed over a steam bath until the orange color is discharged. The solvent is removed and oily residue is recrystallized from hexane. 6.6 g (73% yield) of title compound is obtained, having a melting point of 62°-4° C.

Analysis for: $C_{17}H_{14}ClNO_2S_2$; Calculated: C, 56.11; H, 3.88; N, 3.85; Found: C, 56.05; H, 3.92; N, 3.84.

EXAMPLE 9

α-(5-Chlorobenzothiazol-2-ylthio)-α phenylacetamide

To 6.0 g (0.189 m) of the compound of Example 6 in 300 ml methylene chloride is introduced gaseous ammonia. The orange solid dissolves with discharge of the orange coloration followed by the precipitation of a white solid. After 15 minutes, the introduction of ammonia is stopped and the mixture is stirred for 30 minutes. The solid is collected and a further quantity of solid is recovered upon removal of the solvent from the filtrate. The combined solids are recrystallized from acetonitrile to give 5.0 g (79% yield) of title compound having a melting point of 181°-3° C.

Analysis for: $C_{15}H_{11}ClN_2OS_2$; Calculated: C, 53.80; H, 3.31; N, 8.37; Found: C, 53.67; H, 3.41; N, 8.44.

EXAMPLE 10

α-[(5-Chloro-2-benzothiazolyl)thio]-N-(2-hydroxyethyl)benzene acetamide 6.2 g (0.02 m) of the compound of Example 6 and 1.2 g (0.02 m) ethanolamine in a methylene chloride solution are warmed over a steam bath until dissolution is complete and the coloration discharged. The solution is filtered and the solvent removed. The residue is triturated with ether, the solid is collected and dried in a drying oven. 6.2 g (82% yield) of title compound, having a melting point of 148°-9° C., is obtained.

Analysis for: $C_{17}H_{15}ClN_2O_2S_2$; Calculated: C, 53.88; H, 3.99; N, 7.40; Found: C, 54.03; H, 4.14; N, 7.46.

EXAMPLE 11

α-[(5-Chloro-2-benzothiazolyl)thio]acetic acid, [2-(acetylamino)ethyl]ester 3.18 g (0.01 m) of the compound of Example 6 and 1.03 g (0.01 m) N-acetylethanolamine are dissolved in methylene chloride and the solution is heated to reflux for 3 days. After removal of the solvent, the oily residue is recrystallized from 100 ml ether. 3.5 g (83% yield) of title compound, having a melting point of 107°-8° C., is obtained.

Analysis for: $C_{19}H_{17}ClN_2O_3S_2$; Calculated: C, 54.21; H, 4.07; N, 6.66; Found: C, 53.95; H, 4.14; N, 6.59.

EXAMPLE 12

α-[(5-Chloro-2-benzothiazolyl)thio]benzeneethanethioic acid, S-[2-(2-naphtalenylamino)-2-oxoethyl]ester 3.18 g (0.01 m) of the compound of Example 6 and 2.17 g (0.01 m) α-mercapto-N-(2-naphthyl)acetamide are dissolved in methylene chloride and the mixture is heated to reflux for 7 days. The progress of the reaction is monitored by TLC. After removal of solvent, the residue is recrystallized from ether. 2.3 g (42% yield) of title compound, having a melting point of 144°–5° C., is obtained.

Analysis for: $C_{27}H_{19}ClN_2O_2S_3$; Calculated: C, 60.60; H, 3.58; N, 5.24; Found: C, 60.89; H, 3.78; N, 5.27.

EXAMPLE 13

α-[(5-Chlorothiazolo[5,4-b]pyridin-2-yl)thio]α-phenyl acetic acid

A methylene chloride solution of 4.05 g (0.02 m) 5-chloro-2-mercaptothiazolo[5,4-b]pyridine, 4.30 g (0.02 m) α-bromophenylacetic acid and 4.0 g (0.04 m) triethylamine is heated to gentle reflux overnight. The methylene chloride solution is extracted twice with a dilute hydrochloric acid solution and once with water and then dried over anhydrous MgSO₄. After the solvent is removed, the residual solid is recrystallized from acetonitrile. 5.0 g (74% yield) of title compound, melting at 175°–7° C., is obtained.

Analysis for: $C_{14}H_9ClN_2O_2S_2$; Calculated: C, 49.92; H, 2.69; N, 8.32; Found: C, 49.97; H, 2.85; N, 8.37.

EXAMPLE 14

α-[(5-Chlorothiazolo[5,4-b]pyridin-2-yl)thio]-α-(p-chlorophenyl)acetic acid

A methylene chloride solution of 6.0 g (0.03 m) of 5-chloro-2-mercaptothiazolo[5,4-b]pyridine, 7.5 g (0.03 m) α-bromo-α-(p-chlorophenyl) acetic acid and 6.0 g (0.06 m) triethylamine is heated to gentle reflux overnight. The solution is extracted twice with a dilute hydrochloric acid solution and then once with water. After drying over anhydrous MgSO₄, the solvent is removed and the residual solid is recrystallized from acetonitrile. 7.5 g (68% yield) of title compound, melting at 144°–6° C., is obtained.

Analysis for: $C_{14}H_8Cl_2N_2O_2S_2$; Calculated: C, 45.29; H, 2.17; N, 7.55; Found: C, 44.87; H, 2.27; N, 7.59.

EXAMPLE 15

α-Phenyl-α-[(4,5,6,7-tetrahydrobenzothiazol-2-yl)thio]acetic acid

A methylene chloride solution of 5.13 g (0.03 m) 2-mercapto-4,5,6,7-tetrahydrobenzothiazole, α-bromophenylacetic acid and 6.0 g (0.06 m) triethylamine is heated to gentle reflux overnight. The solution is extracted twice with a dilute hydrochloric acid solution, once with water and is then dried over anhydrous MgSO₄. The residual solid after solvent removal is recrystallized from acetonitrile. 7.0 g (77% yield) of title compound, melting at 118°–20° C., is obtained.

Analysis for: $C_{15}H_{15}NO_2S_2$; Calculated: C, 58.99; N, 4.95; N, 4.59; Found: C, 59.0; H, 4.94; N, 4.52.

EXAMPLE 16

α-[(6-Nitro-2-benzothiazolyl)thio]benzeneacetic acid

A methylene chloride solution of 5.0 g (0.235 m) 2-mercapto-6-nitrobenzothiazole, 5.2 g (0.235 m) α-bromophenylacetic acid and 5.0 g (0.05 m) triethylamine is heated to gentle reflux overnight. The solution is washed twice with a dilute hydrochloric acid solution and once with water. The solution is dried over anhydrous MgSO₄ and then concentrated. The residue is recrystallized once from benzene and then from acetonitrile. 1.5 g (18% yield) of title compound, having a melting point of 152°–5° C., is obtained.

Analysis for: $C_{15}H_{10}N_2O_4S_2$; Calculated: C, 52.01; H, 2.91; N, 8.09; Found: C, 51.72; H, 2.97; N, 8.01.

EXAMPLE 17

The compounds used in the invention are tested for collagenase inhibition in an in vitro assay based on the procedure described by A. Sellers and J. J. Reynolds, *Biochem. J.*, 167 (1977) pp. 353–60.

Collagenase produced by normal human leukocytes or by normal human skin fibroblasts in cell cultures is purified by absorption onto a collagen Sepharose 4B column. Prior to use in the assay, the zymogen is activated with trypsin, while the trypsin in turn, is inactivated with an excess of soybean trypsin inhibitor.

According to the assay procedure, microfuge tubes are prepared containing a total of about 150 μl. of solution containing: 25 μl collagen ($^{14}$C-acetylated collagen-2 mg/ml in 0.01% acetic acid); 25 μl. of 0.15 M tris/0.015 M CaCl₂, pH 7.4; 75 μl. collagenase in tris buffer (0.05 M tris/0.005 M CaCl₂, pH 7.4); 25 μl of collagenase inhibitor in tris buffer. Samples and controls are incubated at 35° C. for five to eighteen hours depending upon potency of the enzyme. At the end of the reaction period, the tubes are spun down in a Beckman Microfuge. A 25 μl. aliquot of each tube is then assayed in a scintillation counter. Since native collagen forms insoluble fibrils under these conditions, radioactivity detected in the supernate is a measure of collagen hydrolysis.

In a set of experiments, the compound α-(5-chlorobenzothiazol-2-ylthio)-benzene acetic acid is tested in the assay to determine its collagenase inhibition activity. The results are summarized below.

| Experiment Number | Concentration of compound (M) | % Collagenolysis |
| --- | --- | --- |
| 1 | 0 | 67 |
|   | $5 \times 10^{-4}$ | 28 |
| 2 | 0 | 70 |
|   | $1.0 \times 10^{-4}$ | 50 |

The results show that the compound tested is able to significantly reduce collagenolysis at low levels of compound concentration.

What is claimed is:

1. A method of inhibiting collagenase in mammals afflicted with a disease state in which collagen is broken down by collagenase, which comprises administering to such an afflicted mammal an amount sufficient to reverse said collagenase-induced collagen break down of a collagenase inhibitor having the formula:

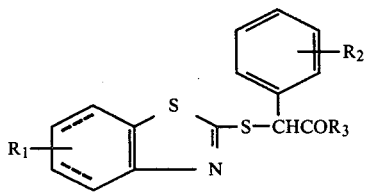

wherein $R_1$ is hydrogen, halo, nitro, amino, lower alkyl, lower alkoxy, trifluoromethyl or hydroxy; $R_2$ is fluorine, chlorine, bromine, lower alkyl, lower alkoxy, amino, nitro or trifluoromethyl; $R_3$ is hydroxy, lower alkoxy, amino, hydroxy(lower)alkylamino, N-(lower)alkanoylamino(lower)alkoxy or N-arylcarbamoyl(lower)alkylthio; and where the dotted lines represent optional double bonds in the 5,6- and 7,8-positions, and the pharmacologically acceptable salts thereof.

2. The method of claim 1, wherein the inhibitor is α-(2-benzothiazolylthio)benzeneacetic acid.

3. The method of claim 1, wherein the inhibitor is α-(5-chlorobenzothiazol-2-ylthio)benzeneacetic acid.

4. The method of claim 1, wherein the inhibitor is the sodium salt of α-(5-chlorobenzothiazol-2-ylthio)benzeneacetic acid.

5. The method of claim 1, wherein the inhibitor is α-(5-chlorobenzothiazol-2-ylthio)-α-(p-chlorophenyl)acetic acid.

6. The method of claim 1, wherein the inhibitor is α-(p-chlorophenyl)-α-(benzothiazol-2-ylthio)acetic acid.

7. The method of claim 1, wherein the inhibitor is α-(5-chloro-2-benzothiazolylthio)benzene acetic acid, ethyl ester.

8. The method of claim 1, wherein the inhibitor is α-(5-chlorobenzothiazol-2-ylthio)-α-phenylacetamide.

9. The method of claim 1, wherein the inhibitor is α-[(5-chloro-2-benzothiazolyl)thio]-N-(2-hydroxyethyl)benzeneacetamide.

10. The method of claim 1, wherein the inhibitor is α-[(5-chloro-2-benzothiazolyl)thio]acetic acid, [2-(acetylamino)ethyl]-ester.

11. The method of claim 1, wherein the inhibitor is α-[(5-chloro-2-benzothiazolyl)thio]benzeneethanethioc acid S-[2-(2-naphthalenylamino)-2-oxoethyl]ester.

12. The method of claim 1, wherein the inhibitor is α-phenyl-α-[(4,5,6,7-tetrahydrobenzothiazol-2-yl)thio]acetic acid.

13. The method of claim 1, wherein the inhibitor is α-[(6-nitro-2-benzothiazolyl)thio]benzeneacetic acid.

* * * * *